United States Patent [19]

Mann

[11] Patent Number: 6,030,948

[45] Date of Patent: Feb. 29, 2000

[54] HAIR REGENERATION COMPOSITIONS FOR TREATMENT OF ALOPECIA AND METHODS OF APPLICATION RELATED THERETO

[76] Inventor: Morris A. Mann, 21669 W. 57$^{th}$ Ave., Glendale, Ariz. 85308

[21] Appl. No.: 08/994,347

[22] Filed: Dec. 19, 1997

[51] Int. Cl.$^7$ .................................................. A61K 38/00
[52] U.S. Cl. ............................................ 514/12; 514/880
[58] Field of Search ................................................ 514/12

[56] References Cited

PUBLICATIONS

CA 127:1555, Hoon, et al, J. Dent. Res., 76(4), 831–838, abstract, 1997.

Medline AN 97020262, Moll, et al, Histochemical Journal, 28(1) 45–52, abstract, Jan. 1996.

Medline AN 77057092, Steele, et al, Pedeatric Res., 10(12), 1003–5, abstract, Dec. 1976.

*Primary Examiner*—Rebecca Cook
*Attorney, Agent, or Firm*—Seed and Berry LLP

[57] ABSTRACT

Hair regeneration compositions containing T$\alpha$1, T$\beta$4, or a combination thereof for treating alopecia on the scalp of a patient in need thereof are disclosed. Teatment methods include (1) cleansing the scalp with a cleansing agent; (2) treating the cleansed scalp with a keratin solvent system; (3) applying a topical anesthetic (optional); (4) applying an acid peel solution; (5) applying a hyperactive urea gel formula (optional) and (6) applying a hair regeneration composition.

28 Claims, 1 Drawing Sheet

HAIR REGENERATION COMPOSITIONS FOR TREATMENT OF ALOPECIA AND METHODS OF APPLICATION RELATED THERETO

TECHNICAL FIELD OF THE INVENTION

The present invention generally relates to compositions and methods for the treatment of alopecia.

BACKGROUND OF THE INVENTION

Alopecia has been a problem afflicting mankind and animals for thousands of years. In many individuals, alopecia causes embarrassment, psychological problems, including depression, and can affect one's self image and feelings of sexuality. Alopecia has been hypothesized to have various etiologies in males and females, many of which involve gonadal steroids. Alopecia is more common in men (e.g., male pattern baldness or androgenic alopecia) than in women (e.g., female pattern baldness). Cosmetic research has devoted millions of dollars and countless hours of research to solve this problem.

In itself, hair loss is a natural phenomenon. Hair growth follows a cycle which involves the birth and development of the follicle, a stationary phase, and a final phase during which the hair is expelled. This alternation between the phases of growth (the anagenic phase), regression (the catagenic phase), and the rest (the telegenic phase) is due to the specific secretion of the hair follicle which acts as a gland, and progressively produces a mass of keratin which it eliminates and replaces after a resting period. The cycle begins the development of the hair follicle that rises up from the dermis which contains large numbers of mesenchymatous cells, resulting in the formation of a dermal papilla. In the final stage (the anagenic phase) the cells surrounding the dermic papilla divide actively every 12 hours in order to produce cells which line up, grow longer, and begin to keratinize. This is hair growth. During the catagenic phase mitosis no longer occurs and the bulb detaches itself from the papilla and rises towards the surface. In the telogenic phase the hair is fully keratinized and is ready to be expelled. After three to four months, another mitotic cycle begins in the germination zone of the hair and another hair follicle is formed.

Although a variety of techniques have been employed to treat alopecia, there remains a need in the art for methods and compositions for this purpose. The present invention fulfills this need and provides further related advantages.

SUMMARY OF THE INVENTION

The present invention provides a methodology that is effective for the treatment of alopecia, and is based on the discovery that the primary cause of all alopecia in humans and other warm-blooded mammals is a decrease in cell-mediated immunity. Since puberty is related to an increase in androgens and estrogens, and since alopecia androgenetica very rarely starts prior to puberty, hormonal factors are involved. It is known that deficiencies in cell-mediated immunity are directly responsible for alopecia areata and alopecia totalis. It is also known that the thymus gland, which regulates cell-mediated immunity, involutes at puberty. It was subsequently hypothesized that there was a high degree of likelihood that an infectious agent was responsible for hair loss. Hair loss rarely occurs without inflammation. Therefore, investigations were undertaken to determine the cause of the inflammation responsible for the various forms of alopecia. In order to determine the infectious agent, chemical systems that solubilize keratin and chemical systems that induce substantial exfoliation were developed.

It has surprisingly been determined that a fungus is responsible for virtually all cases of hair loss. This fungus resides at the dermal/epidermal junction and is clearly apparent with Wood's lamp (UV) radiation. Cultures of the scalp reveal that this fungus is a trichophyton species with a variation that is sex determined. The type of fungus that lives on the male scalp is genetically different from the type of fungus that lives on the female scalp. While not wanting to be bound by this theory, it is believed that this fungus is the primary factor for hair loss. Equally surprising is the discovery that this fungus is spread by an ecto-parasite. This parasitical organism has been isolated, analyzed under the microscope and found to be of the species *demodicidea*. To date, this parasitical organism has been found in all test subjects who are experiencing hair loss.

The present invention provides compositions and methods to resolve the fungal infection problem and eliminate the ecto-parasite, thereby treating alopecia on the scalp of a warm-blooded animal in need thereof, including humans (collectively referred to herein as a "patient"). As used herein, the phrase "treating alopecia" means stimulating and/or regenerating hair growth by topical application of an effective amount of a hair regeneration composition of this invention. As used herein, the term "effective amount" means an amount of the hair regeneration composition which stimulates and/or regenerates hair growth associated with a hair-loss affiliations (such as male pattern baldness).

Hair regeneration compositions of this invention contain Tα1 and/or Tβ4 and may optionally contain a steroid, an indole-based compound, a mitocide, a bioflavanoid, an anti-fungal material, an anti-inflammatory fatty acid and/or a skin absorption enhancer.

As used herein, Tα1 and Tβ4 are isolated extracts of thymosin fraction 5; a steroid includes tamoxifen citrate, progesterone, pregnenolone, spironolactone, pregneaolone, dehydroepiandrosterone (DHEA), diosgenin, triphenylethylene based compounds and/or testolactone; an indole-based compound includes indole, melatonin, N-[2-(5-Methoxy-1H-indol-3-yl)ethyl]acetamide, skatole, and/or indole-3-carbinol; a mitocite is a solution of surfactant, fragrance and skin penetrant, wherein the skin penetrant includes PX-13, the surfactant includes GEMTEK surfactant (GEMTEK is a proprietary non-ionic surfactant that comprises an alkyloxypolyethyleneoxyethanol, a non-ionic alcohol ethoxylate surfactant, monoethanolamine, tall oil fatty acids, an alkylopolyglycoside surfactant, a tetrasodium salt of ethylenediaminetetraacetic acid (EDTA), with the balance being deionized water), and the fragrance includes menthol, benzyl alcohol, eugenol, phenoxyethanol, isopropyl palmitate, isopropyl myristate, benzyl salicylate, phenylethyl salicylate, thymol, isoamyl salicylate, phenylethyl salicylate, TRITON X-100 surfactant (TRITON X-100 is a octoxynol-9), benzoic acid, benzyl benzoate, methyl salicylate, phenol, oleic acid, caproic acid, and/or carbaryl; a bioflavanoid includes querretin methyl chalcone; an anti-fungal material includes undecylenic acid, griseofulvin, terbinafine and/or an azole compound; an anti-inflammatory fatty acid includes TES TRIOLATE (TES TRIOLATE is a tris-oleoyltromethamine ethane sulphate phospolipase A-2 inhibitor) and/or PX-13; and a skin absorption enhancer includes khellin, methyl nicotinate, MSM-Decy methyl sulfoxide, diethylene glycol, citric acid, pyruvic acid, phenoxyethanol, transcutol, GEMTEK surfactant, phosphatidyl choline, MCT oil and/or water.

The methods of this invention for treating alopecia include the steps of cleansing the scalp of a patient with a cleansing agent; treating the cleansed scalp with a keratin solvent system; applying an acid peel solution to the keratin treated scalp; and applying a hair regeneration composition of this invention to the acid peeled scalp. The methods of this invention further include the optional step of applying a topical anesthetic after the scalp has been treated with the keratin solvent system but before the acid peel solution has been applied. Such topical anesthetics preferably include a surfactant that will enhance penetration and a solubilization composition which will facilitate penetration. A further optional step includes application of a hyperactive urea gel formulation to solubilize bumps present on the surface of the scalp. This optional step is performed after the acid peel solution has been applied, but before application of the hair regeneration composition.

Cleansing of the scalp may be accomplished with a cleansing shampoo that includes a hard-surface ethoxylated cleanser, GEMTEK solution. The keratin solvent system includes a urea-based solution, an acetic acid-based solution and/or a urea gel formulation, wherein the urea gel formulation includes urea, citric acid, urea-peroxide, propylene glycol, ethoxylated alcohol and acrylic acid copolymer. The acid peel solution includes a physiological acid. The optional surfactant and solubilization composition includes GEMTEK surfactant. The optional hyperactive urea gel formulation includes urea, citric acid, urea-peroxide, 2-phenoxyethanol, propylene glycol, GEMTEK SC-1000 and/or ethyoxydiglycol.

These and other aspects of this invention will be evident upon reference to the following detailed description.

DETAILED DESCRIPTION OF THE INVENTION

As mentioned above, the present invention discloses compositions and methods for the treatment of alopecia by topical administration of a hair regeneration composition to the scalp of a patient in need thereof. Administration of the hair regeneration composition of the present invention may be accomplished in any manner which will result in the delivery of an effective amount of the hair regeneration composition to the animal, including delivery to the hair follicles. For example, administration may be by topical application directly to the scalp, or other area where hair stimulation is desired.

The hair regeneration composition is formulated for topical administration. Suitable topical formulations include one or more hair regeneration compositions in the form of a liquid, lotion, cream or and gel. Topical administration may be accomplished by application directly on the scalp or other area. For example, such application may be accomplished by rubbing the formulation (such as a lotion or gel) onto the skin of the scalp, or by spray application of a liquid formulation. Any quantity of the topical formulation sufficient to accelerate the rate of hair growth is effective, and treatment may be repeated as often as the progress of hair growth indicates.

Accordingly, in one embodiment of the present invention, a hair regeneration composition is provided which includes, as an active component thereof, certain extracts of thymosin, specifically an extract referred to as thymosin fraction 5.

Other components which may also be present in the hair regeneration composition of this invention include a steroid, an indole-based compound, a mitocide, a bioflavanoid, an antifungal material, an anti-inflammatory fatty acid and a skin absorption enhancer. Each of the above components are set forth in further detail below.

Thymosin Fraction 5

Figure 1:
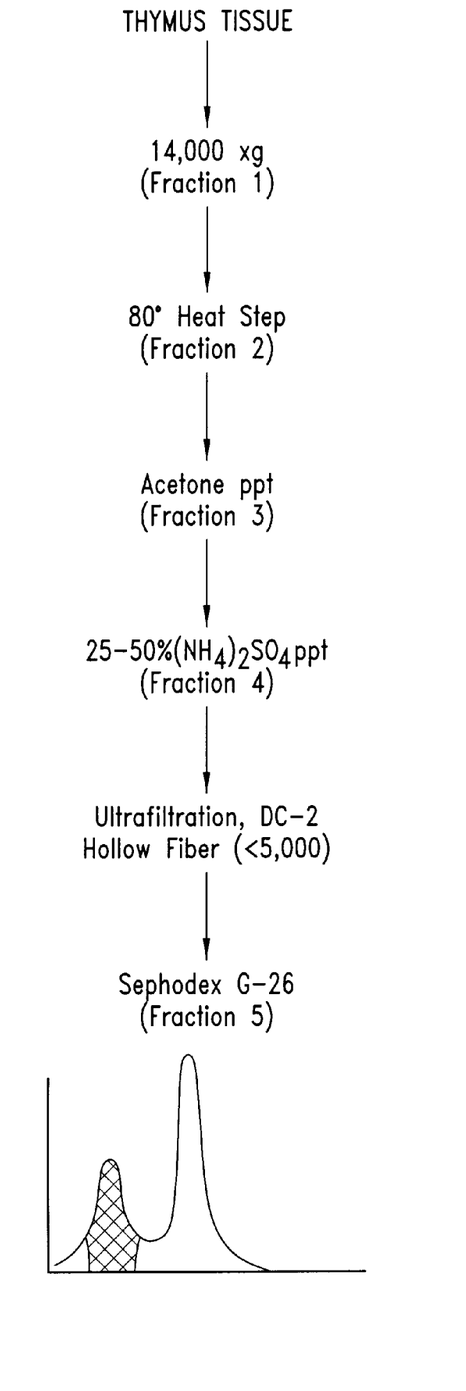
The FIGURE illustrates purification of Thymosin fraction 5 from thymus tissue.

Thymosin fraction 5 (TF5) is a partially purified mixture of polypeptides prepared from calf thymus glands. TF5 has been routinely prepared from calf thymus. However, it may also be prepared from porcine, ovine, murine, goat, rat, chicken, and human thymus tissues. Preparation and isolation of TF5 have been described (Hooper et al., "The purification and properties of bovine thymosin," *Ann. NY Acad. Sci.* 249:125, 1975). A representative purification strategy is illustrated in the FIGURE. TF5 consists of at least 40 to 50 distinct polypeptides on isoelectric focusing on polyacrylamide gel plates (pH 3.5–9.5). TF5 is essentially free of lipids, carbohydrates and endotoxins. TF5 has been demonstrated to be effective in reconstituting immune functions in thymic-deprived or immunodeprived animals, in humans with primary immunodeficiencies, and in immunosuppressed cancer patients. A primary effect of this mixture of peptides is to stimulate cell-mediated immunity.

Two of the major biologically active ingredients in TF5 are thymosin $\alpha 1$ (T$\alpha 1$) an immunomodulatory peptide of 28 amino acids (molecular weight 3,108 daltons) (Low et al., "The chemistry and biology of Thymosin I. Isolation and characterization and biological activities of T$\alpha_1$ and polypeptide $\beta_1$ from calf thymus," *J. Bio. Chem.* 254:981, 1979), and thymosin $\beta 4$ (T$\beta 4$), an actin-sequestering peptide of 43 amino acids (molecular weight 4,963 daltons) (Low, T. L. K., and Goldstein, A. L., "Chemical characterization of thymosin $\beta_4$," *J. Bio. Chem.* 257:1000, 1982). T$\alpha 1$ and T$\alpha 4$ are highly conserved in nature and their amino acid sequences are identical in most mammalian species. More than a dozen TF5-like preparations have been prepared from calf or porcine thymus tissue. These thymic extracts such as thymostimulin (TP-1), TFX, thymalin, thymoject, thym-Uvocal, and others, are variations of the TF5 formulation and are all partially purified preparations composed primarily of polypeptide mixtures with molecular weights of 15,000 or less. The major biologically active components of TF5 contain T$\alpha 1$ and T$\beta 4$, as well as lower concentrations of other purified well characterized thymosin peptides such as prothymosin a (Pro T$\alpha 1$), T$\alpha 2$ to T$\alpha 11$ and T$\beta 3$, T$\beta$ to T$\beta 13$, MB3S, MB40, ubiquitin, thymulin (FTS), thymic humoral factor (THF$\alpha 2$) and thymopoietin (TP). The TF5-like extracts prepared by variations of the procedure used originally to prepare TF5 may also contain $\alpha$ and $\beta$ as key ingredients and smaller quantities of the other peptides described in TF5 such as Pro T$\alpha 3$, FTS, THF$\alpha 2$, TP, ubiquitin and MB 35 and MB 40.

The present invention includes TF5 and all TF5-like thymic extracts that contain T$\alpha 1$ and/or T$\beta 4$. T$\alpha 1$ and T$\beta 4$ have been characterized with regard to their ability to stimulate and regulate cell-mediated immunity, to enhance wound healing, and for their ability to increase resistance to microbial infections and to decrease microbial adherence (Baumann et al., Preclinical studies of thymosin $\alpha_1$ and thymosin $\beta_4$, In: Mauer, H. R., Goldstein, A. L., Hager, E. D., Thymic peptides in preclinical and clinical medicine, W. Zuckschwerdt Verlag Munchen, Bern, Wien, New York, pp. 13–17, 1977). The terms TF5 or TF5-like, as used in the present application, refer only to those thymic extracts that include T$\alpha 1$ and/or T$\beta 4$. Although other peptides may be present in some concentration in TES or TFS-like preparations, the presence of Tα1 and/or Tβ4 in the TF5 or TF5-like preparation is required for use in the present invention, and preferably at a concentration ranging from 0.05 to 0.1% by weight for each Tα1 and/or Tβ4.

The importance of TF5 or TF5-like preparations in preventing infections in immunocompromised patients was first suggested by studies in immunosuppressed animals (Oates, K., Goldstein, A. L., Thymosin. In: De Vita, D. T. Hellman, S., Rosenberg, S. A. (eds.), Biological therapy of cancer, 2nd ed., J B Lipencott, Philadelphia, pp. 705–718, 1995; Goldstein, A. L., "Clinical applications of thymosin alpha-1," Cancer Invest. 12:545–547, 1994). Early studies demonstrated an increased survival rate of immunosuppressed mice infected with BCO, Candida, or Cryptococcus when these animals were treated with TF5, Tα1 or TF5-like preparations (Collins, F. M. and Morrison, N. E., "Restoration of T-cell responsiveness by thymosin: Expression of antituberculosis immunity in mouse lungs," Infect. Immun. 23:330, 1979; Bistoni et al., "Increase of mouse resistance to Candida albicans infection by Thymosin a 1," Infect. Immun. 36(2):609–614, 1982). In T-cell depleted mice, TF5 has been found to restore cellular immunity to Blastomyces dermatitidis (Longley, R. E. and Cozad, G. C., "Thymosin restoration of cellular immunity to Blastomyces dermatitidis in T-cell depleted mice," Infect. Immun. 26(1):187–92, 1979). In similar studies cell-mediated immunity to Listeria monocytogenes was increased in protein malnourished mice following treatment with TF5. The administration of TF5 or Tα1 also stimulated a significant rise in the amount of interferon (IFN) produced in mice infected with the Newcastle disease virus (Huang et al., "Thymosin treatment modulates production of interferon," J. Interferon Res. 1:411, 1981). In similar studies in mice, an injection of TF5 or Tα 1 increased resistance to infection with Candida albicans (Bistoni et al., "Increase of mouse resistance to Candida albicans infection by Thymosin a 1," Infect. Immun. 36(2):609–614, 1982; Salvin, S. B. and Neta, R., "Resistance and susceptibility to infection in inbred murine strains. I. Variations in the response to thymic hormones in mice infected with Candida albicans," Cell Immunol. 75:160, 1983. The increased resistance to infection with an infectious agent after administration of TF5 has been attributed to an increase in the release of specific cytokines such as MIF and IFN (Salvin, S. B. and Neta, R., "Resistance and susceptibility to infection in inbred murine strains. I. Variations in the response to thymic hormones in mice infected with Candida albicans," Cell Immunol. 75:160, 1983). Injection of TF5 and Tα1 has also been shown to protect 5-fluorouracil (5FU)- or morphine-immunosuppressed mice against opportunistic infections with C. albicans, Listeria monocytogenes, Pseudomonas aeruginosa, and Serratia marescens (Ishitsuka et al., "Protective activity of thymosin against opportunistic infections in animal models," Cancer Immunol. Immunother. 14:145, 1983; Di Francesco et al., "Combined effect of flucoazole and thymosin $\alpha_1$ on systemic candidasis in mice immunosuppressed by morphine treatments," Clin. Ex. Immuno. 97:347–352, 1994). The efficacy of Tα1 administered in combination with the antiviral drug amantadine and interferon was also demonstrated in mice infected with the influenza virus. This new combination therapy protocol has been found to significantly increase the long term survival, to reduce viral titers in the lungs, and to restore a number of the immunological parameters tested such as natural killer cell activity, cytotoxic T-lymphocyte responses, and subsets of CD4+/CD8+ lymphocytes (D'Agostini et al., "Efficacy of combination therapy with amantadine, $T\alpha_1$, and $\alpha/\beta$ IFN in mice infected with influenza A virus," Int. J. Immunopharmacol. 18:95–102, 1996).

Clinical studies in humans using various TF5 or TF5-like preparations (e.g., THF, TFX, TP-I) have shown that the administration of thymic factors can shorten the course of viral infections (e.g., herpes zoster, herpes simplex, adenovirus, hepatitis, and cytomegalovirus) and increase the restoration of T-cell immunity in these patients (Ajiuti et al., "A placebo controlled trial of thymic hormone treatment of recurrent herpes simplex labialis infection in immunodeficient host: Results after a 1 year follow up," Clin. Immunol. Immunopathol. 30:11, 1984; Businco, L. and Rezza, E., "Therapy of viral disease in immunosuppressed patients with TP-1," Thymic Hormones and T-lymphocytes (A. F. Wigzel, ed.), Academic Press, New York, p. 295, 1981; Demartino et al., "T-lymphocytes in children with respiratory infections: Effect of the use of thymostimulin on the alteration of T-cell subsets," Int. J. Tissue React. 6:223, 1984; Schulof, R. S. and Goldstein, A. L., "Clinical applications of thymosin and other thymic hormones," Recent Advances in Clinical Immunology (R. A. Thompson and N. R. Rose, eds.), Churchill Livingstone, Edinburgh, p. 243, 1983; Trianin et al., "The role of THF a thymic hormone, as a regulator of T-cell differentiation in humans," Current Concepts in Human Immunology and Cancer Immunomodulation (Serrpu et al., eds.), Elsevier Biomedical, New York, p. 295, 1981). These studies suggest that TF5 or TF5-like preparations may be useful in preventing or attenuating infections in immunocompromised hosts.

TF5 and TF5-like preparations have also been utilized in clinical trials in patients with primary and secondary immunodeficiencies. A number of syndromes related to congenital defects of the immune system are included in this category. These may include T-cell, B-cell or both lymphocyte population defects. An increase in the percentage and numbers of Erosette-forming cells in vitro after incubation with TF5 and TF5-like preparations has been reported (Schulof, R. S. and Goldstein, A. L., "Clinical applications of thymosin and other thymic hormones," Recent Advances in Clinical Immunology (R. A. Thompson and N. R. Rose, eds.), Churchill Livingstone, Edinburgh, p. 243, 1983).

Several thymic preparations, such as TF5, TP-I, TP-5, thymulin, THF, and TPX, have been studied in clinical trials in children with primary immunodeficiency diseases (Goldstein, A. L., "Clinical applications of thymosin alpha-1," Cancer Invest. 12:545–547, 1994, Trianin et al., "The role of THF a thymic hormone, as a regulator of T-cell differentiation in humans," Current Concepts in Human Immunology and Cancer Immunomodulation (Serrpu et al., eds.), Elsevier Biomedical, New York, p. 295, 1981; Bach, J. F. and Dardenne, M. "Clinical aspects of thymulin (FTS)," Thymic Hormones and Lymphokines (A. L. Goldstein, ed.), Plenum Press, New York, p. 593, 1984; Davies, E. G. and Levinsky, R. J., "Experience in the use of thymic hormones for immunodeficiency disorders," Thymic Factor Therapy, Vol. 16 (N. A. Byron and J. R. Hobbs, eds.), Serono Symposium Publications, Raven Press, New York, p. 156, 1984; Goldstein, A. L., "Thymosin alph-1: Chemistry, mechanism of action and clinical applications," Combination Therapies 2 (E. Garaci and A. L. Goldstein, eds.), Plenum Press, New York, pp. 39–48, 1993; Skotnicki et al., "Biological properties and clinical use of calf thymus extract TFX-Polfa," Thymic Hormones and Lymphokines (A. L. Goldstein, ed.), Plenum Press, New York, p. 545, 1984; Wara et al., "Thymosin fraction 5 therapy in patients with primary immunodeficiency disorders," Thymic Factor Therapy, Vol. 16 (N. A. Byron and J. R. Hobbs, eds.), Serono Symposia Publications, Raven Press, New York, p. 123, 1984). These studies indicate that thymic factors are useful in reconstituting cellular immune responses and improving clinical status in these patients.

The Tα1 fraction and the Tβ4 fraction have been completely characterized and are noted for their ability to decrease microbial adherence, enhance wound healing, and stimulate cell-mediated immunity. Thus, topical application of these particular thymic fractions increase the ability of the skin to resist fungal and other infections, and appear to assist the skin's ability to mount a reaction to the fungus and eliminate it. Hair growth has been noted in all cases where the substance has been applied after the treatments previously mentioned.

Steroids

A variety of steroids influence fungal growth. It has been found that the sex steroids dihydrotestosterone (DHT), testosterone, and estradiol protect the hyphae of fungi from humoral attack. DHT is more protective than testosterone which is more protective than estradiol. Other steroids block this effect. These include progesterone, spironolactone, pregnenolone, and dihydroepiandrosterone (DHEA). Relative blocking efficacy is in the aforementioned with progesterone being by far the most powerful. Interestingly enough, diosgenin, a plant-derived progestational analogue, is almost as effective as progesterone.

The final effect of fungal inflammation is an increase in the production of epidermal growth factor (EGF). This is clearly apparent in onychomycosis where one notes an overgrowth of keratin and concomitant thickening of the nail. In hair this results in a narrowing of the pore, through which the hair is growing. The final result is the elimination of terminal hair with replacement by fine lanugo-type hair. The dermal papilla of this time is forced to assume a resting phase. It should also be noted that DHT, testosterone, and estradiol promote the formation of epidermal growth factor. (DHT>testosterone>estradiol).

Substances that block DHT, testosterone, estradiol and EGF are thus believed to be of value in the prevention and treatment of alopecia. Systemic antiestrogens that have been used include tamoxiten citrate, a variety of triphenylethylene-based compounds and testolaotone.

Anti-Fungal Material

The various azoles, especially ketoconazole have been found to have a significant role in the treatment of alopecia. Ketoconazole is important because it also blocks testosterone, DHT, and estrudiol non-specifically. However, systemic treatment to this compound over a long period of time results in loss of libido in men and women. In the context of topical treatment, this problem does not occur, and the effect relative to alopecia is much more significant. Undecylenic acid and a variety of systemic preparations may also be employed. These include grisocfulvia, terbinafine and fluconazole and other azoles, as well as ampotercin B and ampotercin like compounds.

Bioflavanoids and EGF

Surprisingly, bioflavanoids can inhibit the production of epidermal growth factor (EGF). The most powerful of these, quercetin methyl chalcone, is water soluble. This compound effectively blocks EGF in relatively low concentrations. This greatly reduces hair loss and contributes significantly to hair growth. Polyamines also have this ability. Putrescine, protamine, etc., all will promote hair regrowth by blocking EGF. However, these substances are not cosmetically preferable for topical use because of their odor. It has been found that compounds containing bioflavanoids, especially quercetin methyl chalcone, greatly reduce hair loss and facilitate hair regrowth.

Mitocides

The presence of an ectoparasite and its role in alopecia prompted the development of an effective mitocide. Using fragrance-based chemicals, a skin penetrant, preferably PX-13, and a surfactant, it was discovered that this parasite could be effectively eliminated. Concomitantly, it was discovered that this composition was capable of effectively killing any mite, insect or chitin-coated organism. This was completely unexpected. Although others have recognized the efficacy of fragrance moieties in an aerosolized format, the novelty represented by this invention is inherent in the concomitant administration of a surfactant and an antilipase composition (such as PX-13). PX-13 is described in U.S. Pat. No. 5,659,055 incorporated herein by reference.

Quantitative analysis of efficacy was determined with Demodex species. This mite is particularly resistant to common insecticides and mitocides (such as pyrethrins, lindane), and other representative phosphodiesterase inhibitors (such as malathion). Representative in vitro kill times for the various compositions are noted and compared with the preferred example in Table 1. The various fragrance compositions are also noted following Table 1 along with component ranges.

TABLE 1

KILL TIMES FOR DEMODEX IN VITRO

| | | |
|---|---|---|
| 1. Lindane | | 38 min |
| 2. Mixed pyrethrins | | 92 min |
| 3. Malathion | | 27 min |
| 4. Fragrance 1 | | 15 min |
| 5. Fragrance 2 | | 12 min |
| 6. Fragrance 3 | | 17 min |
| 7. PX-13 | | 3 min |
| 8. PX-13 + Fragrances | | <2 min |
| 9. Control oleic acid | | 42 min |
| 10. Control (caprylic/caproic acid) (medium chain triglyceride) | | >45 min |

| | % | Range |
|---|---|---|
| Fragrance I | | |
| Benzoic acid | 15 | 0–80 |
| Benzyl benzoate | 50 | 0–90 |
| Methyl salicylate | 9.5 | 0–100 |
| Phenol | 0.5 | 0–80 |
| Thymol | 5 | 0–80 |
| Eugenol | 5 | 0–80 |
| Benzyl salicylate | 15 | 0–90 |
| Fragrance II | | |
| Benzoic acid | 15 | 0–80 |
| Benzyl benzoate | 50 | 0–90 |
| Isoamyl salicylate | 5 | 0–100 |
| Phenol | 1 | 0–80 |
| Thymol | 4.5 | 0–80 |
| Eugenol | 4.5 | 0–80 |
| Benzyl salicylate | 15 | 0–90 |
| Phenylethyl salicylate | 5 | 0–100 |
| Fragrance III | | |
| Benzoic acid | 15 | 0–80 |
| Benzyl benzoate | 50 | 0–90 |
| Methyl salicylate | 5 | 0–100 |
| Isoamyl salicylate | 5 | 0–100 |
| Phenylethyl salicylate | 5 | 0–100 |
| Benzyl salicylate | 10 | 0–100 |
| Phenol | 0.5 | 0–80 |
| Thymol | 4.5 | 0–80 |

The above ingredients are shown in weight percent, and are available from commercial suppliers such as Brooks, Sigma (St. Louis, Mo.) and Aldrich (Milwaukee, Wis.).

Indole-Based Compounds

Certain indole-based compounds have a significant effect on hair loss. These include but are not limited to indole, skatole, indole-3-carbinol, and melatonin. They exert their effect by blocking the effects of virtually all estrogens. Melatonin has been used in high doses orally as an effective birth control agent, and a combination of indole-3-carbinol and melatonin is more powerful than either alone. Further, these compounds have antifungal properties. It should also be noted that very high concentrations of indole are found in jasmine fragrance and citrus flower based fragrances such as orange and lemon.

Melatonin has been found to alter the cyclic pattern of hair growth in rodents (Houssay, 1966 a,b; Rose et al., 1984). Melatonin compositions and methods of using these melatonin compositions have been developed for treating the cosmetic and physical appearance of the scalp. (Pierpaoli, W., Regelson, W., Melatonin Compositions and Uses Thereof. U.S. Pat. No. 4,746, 674 (1988)).

The effect of melatonin on steroid hormone production has been observed in several systems (Ellis, 1972; Frehn et al., 1974; Ogle & Kitay, 1977). Melatonin was found to increase the 5-alpha reductase of seminiferous tubules for both progesterone and testosterone. Melatonin decreased androgen synthesis in both testicular interstitial cells and tubules. (Ellis, 1972). Currently, 5-alpha reductase modulating agents are being used to treat male pattern baldness.

Melatonin inhibits estrogen-mediated cell proliferation in MCF-7 cancer cells (Cos, S. Blask, D. E., Melatonin Modulates Growth Factor Activity in MCF-7 Human Breast Cancer Cells. J. Pineal Research 17:25–32 (1994). Molis et al. (1995) have shown that melatonin down-regulates estrogen receptor expression. This group also showed that messenger RNA (MRNA) estrogen-receptor-mediated expression is inhibited by melatonin in MCF-7 breast cancer cells (Molis, T. M., Spriggs, L. L. Hill, S. M., Modulation of Estrogen Receptor mRNA Expression by Melatonin in MCF-7 Human Breast Cancer Cells. Mol. Endicrinol. 8: 1681–90 (1994).

The inhibitory mechanism of melatonin relates to effects on cell cycle response resulting from a block to estrogenic growth stimulation, perhaps through effects on estrogen receptor availability (Crespo et al., 1994; Hill et al., 1992).

Melatonin is included in the composition in the present invention. While not wanting to be bound by any particular theory, it is believed that melatonin affects the response of the hair follicle to the effects of estrogens and androgens, thereby inhibiting the fungi that occupy the hair follicle and cause alopecia. Indoles like melatonin possess antifungal activity, as well as bactericidal action, thereby preventing or inhibiting the growth of fungal and other pathogens (Tsotinis et al., 1997). Melatonin may also help prevent hair-loss due to its free radical scavenging activity (Reiter et al., 1997).

Anti-Inflammatory Fatty Acids

Another substance known as TES TRIOLATE, or PX-13 (U.S. Pat. No. 5,659,055) is capable of dramatically decreasing inflammation, and by nature of its structure inhibiting fungal growth. The combination of these substances as a post treatment moiety dramatically enhances hair regeneration.

Skin Absorption Enhancer

A skin absorption enhancer facilitates penetration and solubilization of the hair regeneration composition on the scalp of the patient. A skin absorption enhancer includes khellin, methyl nicotinate, MSM-Decy methyl sulfoxide, diethylene glycol, citric acid, pyruvic acid, phenoxyethanol, transcutol, GEMTEK surfactant, phosphatidyl choline, MCT oil and water.

The following Table 2 provides a range of concentrations of ingredients that may be used in the skin absorption enhancer.

TABLE 2

SKIN ABSORTION ENHANCER

| | |
|---|---|
| Khellin | 0–10 |
| Methyl nicotinate | 0–20 |
| Decy methyl sulfoxide | 0–60 |
| Diethylene glycol | 0–90 |
| Citric acid | 0–45 |
| Pyruvic acid | 0–45 |
| Phenoxyethanol | 0–85 |
| Transcutol | 0–90 |
| GEMTEK surfactant | 0–20 |
| Phosphatidyl choline | 0–10 |
| MCT oil | 0–30 |
| Water | 0–80 |

The above ingredients are shown in weight percent, and are available from commercial suppliers such as Brooks, Sigma (St. Louis, Mo.) and Aldrich (Milwaukee, Wis.).

The following Table 3 provides a preferred formulation of the skin absorption enhancer.

TABLE 3

SKIN ABSORPTION ENHANCER

| | |
|---|---|
| Khellin | 0.1 |
| Methyl nicotinate | 0.2 |
| MSM-Decy methyl sulfoxide | 2 |
| Diethylene glycol | 4 |
| Citric acid | 4 |
| Pyruvic acid | 2 |
| Phenoxyethanol | 6 |
| Transcutol | 4.7 |
| GEMTEK surfactant | 0.25 |
| Phosphatidyl choline | 0.1 |
| MCT oil | 2 |
| Water | 74.65 |

The above ingredients are shown in weight percent, and are available from commercial suppliers such as Brooks, Sigma (St. Louis, Mo.) and Aldrich (Milwaukee, Wis.).

Ecto-Parasite

The secondary problem of the ecto-parasite may be remedied either acutely or chronically. Acute (i.e., rapid) elimination with agents such as carbaryl, lindane, malathion and other irreversible phosphodiesterase inhibitors is a viable approach. However, surprisingly, we found that copper oleate was a more effective agent over the long term, since it affected fungal growth as well as the ecto-parasite. Copper oleate caused instant death of the ecto-parasite in vitro and long-term administration inhibited growth as well. Other antifungal substances that have proven effective include the various azole derivatives, undecylenic acid, and other substances such as $KMnO_4$.

Methodology for the Treatment of Alopecia

In the method of this invention, the following steps are performed in the order noted: (1) cleansing the scalp with a cleansing agent; (2) treating the cleansed scalp with a keratin solvent system; (3) applying a topical anesthetic (optional); (4) applying an acid peel solution; (5) applying a hyperactive urea gel formula (optional) and (6) applying a hair regeneration composition. This procedure has resulted in hair growth in 100% of subjects tested, including individuals with alopecia androgenetica, alopecia totalis, alopecia universalis and alopecia areata. Furthermore, utilizing the methods and compositions of the present invention, all subjects tested have experienced some hair regrowth with terminal hairs.

Step 1: Cleansing of the Scalp

Cleansing of the scalp is the first step in the method of the present invention for treating alopecia. Cleansing implies the use of substances which include, but are not limited to, a variety of different surfactants which are capable of solubilizing steroid structures. The most effective of these is the GEMTEK solution, which is a proprietary composition, developed and sold by Gemtek (Phoenix, Ariz.). This composition is a hard surface ethoxylated cleanser, which is capable of solubilizing even lanolin. It is mixed in conjunction with a number of other currently available surfactants. This combination has been found to very effectively solubilize virtually all steroid based structures.

A representative cleansing shampoo of this invention is set forth in Table 4.

TABLE 4

| CLEANSING SHAMPOO | |
|---|---|
| Demineralized water | 20.0–50.0 |
| Ethoxylated alcohols (Gemtek solution) | 0.2–5.0 |
| Sodium laureth sulfate | 5.0–25.0 |
| Tea lauryl sulfate | 5.0–25.0 |
| Cocamidopropyl betaine | 2.0–10.0 |
| Cocamide DEA | 1.0–5.0 |
| Citric acid | 0.1–1.0 |
| Tetrasodium EDTA | 0.1–2.0 |
| Quaternized acetamide MEA | 0.1–5.0 |
| POLYSORBATE-60 | 0.1–5.0 |
| POLYSORBATE-80 | 0.1–5.0 |
| PEG-PPG block copolymer | 0.01–5.0 |
| Fragrance | As required |
| Preservative | As required |
| Colorants | As required |

The above ingredients are shown in weight percent, and are available from commercial suppliers such as Brooks, Sigma (St. Louis, Mo.) and Aldrich (Milwaukee, Wis.), except for the ethoxylated alcohols which were obtained from Gemtek (Phoenix, Ariz.).

Step 2: Application of Keratin Solvent System

After utilizing an appropriate surfactant-based material to cleanse the scalp or other afflicted area, a keratin solvent system is applied. Keratin solvent systems include either urea, which can effectively solubilize keratin, or acetic acid based solutions which can solubilize keratin. However, it should be noted that there is a margin of safety with urea, which is not present with acetic acid. Therefore, a urea based solution has been used more extensively. Keratin solvent systems of the present invention comprise urea gel formulation, hyperactive urea gel formulation, and also acetic acid-based solutions.

Acetic Acid Based Formula

The following Table 5 provides a range of concentrations of ingredients that may be used in the acetic acid based solution.

TABLE 5

| ACETIC ACID BASED FORMULA | |
|---|---|
| Acetic acid | 0.1–100 |
| Propylene glycol | 0.1–99 |
| PEG-40 | 0.1–99 |
| Phenoxyethanol | 0.1–99 |
| TERGITOL 1557 | 0.1–90 |
| PEG-400 | 0.1–99 |

The above ingredients are shown in weight percent, and are available from commercial suppliers such as Brooks, Sigma (St. Louis, Mo.) and Aldrich (Milwaukee, Wis.).

The following Table 6 provides a preferred formulation of the acetic acid based solution.

TABLE 6

| ACETIC ACID BASED FORMULA | |
|---|---|
| Acetic acid | 15 |
| Propylene glycol | 50 |
| PEG-40 | 12 |
| Phenoxyethanol | 6 |
| TERITAL 1557 | 1 |
| PEG-400 | 16 |

The above ingredients are shown in weight percent, and are available from commercial suppliers such as Brooks, Sigma (St. Louis, Mo.) and Aldrich (Milwaukee, Wis.).

Urea Based Gel Formula

The following Table 7 provides a range of concentrations of ingredients that may be used in the urea gel formulation.

TABLE 7

| UREA GEL FORMULA | |
|---|---|
| Urea reagent grade | 1.0–40.0 |
| Citric acid NF | 0.1–10.0 |
| Urea-peroxide | 0.1–5.0 |
| Propylene glycol NF | 20.0–90.0 |
| Ethoxylated alcohols | 2.0–20.0 |
| Acrylic acid copolymer | 0.1–1.0 |
| Add abrasive polyethylene beads | 0.1–10 |

The above ingredients are shown in weight percent, and are available from commercial suppliers such as Brooks, Sigma (St. Louis, Mo.) and Aldrich (Milwaukee, Wis.).

Optional Step 3: Fragrance-Based Topical Anesthetic.

Next, it is helpful to apply a unique fragrance based topical anesthetic prior to the topical administration of the acid peel solution because the topical anesthetic greatly diminished the discomfort of the acid peel solution. This composition also facilitated penetration of the acid solution, and surprisingly it demonstrated in vitro antifungal and antiparasitic properties. This composition quantifiably decreased discomfort by 60% or more, and increased penetration by 35% as measured by fluorescein dye technology.

A representative fragrance-based anesthetic is set forth in Table 8

TABLE 8

| ANESTHETIC FRAGRANCE | |
|---|---|
| Menthol | 0–50 |
| Benzyl alcohol | 0–80 |
| Eugenol | 0–50 |
| Phenoxyethanol | 0–80 |
| Isopropyl palmitate | 0–80 |
| Isopropyl myristate | 0–80 |
| Benzyl salicylate | 0–50 |
| Phenylethyl salicylate | 0–50 |
| Thymol | 0–50 |
| Isoamyl salicylate | 0–50 |
| TRITON X-100 surfactant | 0–50 |

The above ingredients are shown in weight percent, and are available from commercial suppliers such as Brooks, Sigma (St. Louis, Mo.) and Aldrich (Milwaukee, Wis.).

The following Table 9 provides a preferred formulation of the anesthetic fragrance.

TABLE 9

ANESTHETIC FRAGRANCE

| | |
|---|---|
| Menthol | 9.5 |
| Benzyl alcohol | 19 |
| Eugenol | 0.95 |
| Phenoxyethanol | 19 |
| Isopropyl palmitate | 19 |
| Isopropyl myristate | 19 |
| Benzyl salicylate | 1.42 |
| Phenylethyl salicylate | 1.42 |
| Thymol | 4.75 |
| Isoamyl salicylate | 1.21 |
| TRITON X-100 surfactant | 4.75 |

The above ingredients are shown in weight percent, and are available from commercial suppliers such as Brooks, Sigma (St. Louis, Mo.) and Aldrich (Milwaukee, Wis.).

Step 4: Acid Peel Systems

Application of the optional fragrance-based topical anesthetic is followed by the application of an acid-based system with the composition shown in Table 6. This composition included a series of physiological acids, including citric acid and pyruvic acid, in combination with a surfactant that will enhance penetration and a solubilizing system which also facilitates penetration. The acid peel system is allowed to remain on the scalp for anywhere between 1 minute to 8 hours or more. If the acid peel system is allowed to remain on the scalp for more than about 30 minutes, an occlusive cap may be placed on the head covering the scalp. As used herein, an occlusive cap means any structure, which when placed on the scalp of the head, prevents the acid peel system from leaving the surface of the scalp.

The following Table 10 provides a range of concentrations of ingredients that may be used in the acid peel solution.

TABLE 10

ACID PEEL

| | |
|---|---|
| Citric acid - NF | 2.0–30.0 |
| Salicylic acid - NF | 1.0–20.0 |
| Methyl salicylate | 1.0–20.0 |
| 1-Menthol | 0.1–10.0 |
| POLYSORBATE-80 | 0.1–10.0 |
| 2-Phenoxyethanol | 0.5–10.0 |
| Pyruvic acid | 0.1–20.0 |
| TERGITOL 15-S-7 (TERGITOL 15-S-7 is a proprietary polythylene glycol fatty alcohol ether and a non-ionic surfactant) | 0.1–5.0 |
| Methyl nicotinate | 0.1–1.0 |
| Ethyl alcohol, SD-40 | 10.0–50.0 |
| Demineralized water | 10.0–50.0 |

The above ingredients are shown in weight percent, and are available from commercial suppliers such as Brooks, Sigma (St. Louis, Mo.) and Aldrich (Milwaukee, Wis.).

A representative acid peel system is set forth in Table 11.

TABLE 11

ACID PEEL

| | |
|---|---|
| Citric acid | 20.00 |
| Salicylic acid | 10.00 |
| Methyl salicylate | 10.00 |
| Menthol | 1.00 |
| POLYSORBATE-80 | 3.00 |
| 2-Phenoxyethanol | 6.00 |
| Pyruvic acid | 10.00 |
| TERGITOL 15-S-7 | 1.00 |

TABLE 11-continued

ACID PEEL

| | |
|---|---|
| Methyl nicotinate | 0.50 |
| Alcohol SD40 A (190) | 23.00 |
| Demineralized water | 15.50 |

The above ingredients are shown in weight percent, and are available from commercial suppliers such as Brooks, Sigma (St. Louis, Mo.) and Aldrich (Milwaukee, Wis.).

Optional Step 5: Application of Hyperactive Urea Gel Formula

The hyperactive urea gel formulation is effective in solubilizing bumps present on the surface of the scalp prior to application of the hair regeneration composition. The following Table 12 provides a preferred formulation of the hyperactive urea gel.

TABLE 12

HYPERACTIVE UREA GEL FORMULA

| | |
|---|---|
| Urea | 20.00 |
| Citric acid | 4.00 |
| Urea-peroxide | 1.00 |
| 2-Phenoxyethanol | 15.00 |
| PLURONIC F-127 (PLURONIC F-127 is a proprietary methyloxirane polymer and a non-ionic surfactant) | 3.00 |
| Propylene glycol | 41.00 |
| GEMTEK SC-1000 (GEMTEK SC-1000 is a proprietary non-ionic surfactant that alkyloxypolyethyleneoxyethanol, a non-ionic alcohol ethoxylate surfactant, monethanolamine, tall oil fatty acids, an alkylopolyglycoside surfactant, a tetrasodium salt of ethylenediaminetetraacetic acid (EDTA), with the balance deionized water) | 10.00 |
| Ethoxydiglycol | 5.00 |
| Polyethylene beads | 1.00 |

The above ingredients are shown in weight percent, and are available from commercial suppliers such as Brooks, Sigma (St. Louis, Mo.) and Aldrich (Milwaukee, Wis.).

Step 6: Application of Hair Regeneration Composition

The substances used in the hair regeneration composition of the present invention are typically different for men and women. The men's composition does not contain progestational agents, whereas the female composition contains such agents. Inclusion of T$\alpha$1 and/or T$\beta$4 in the composition assists in boosting cell-mediated immunity.

The following Table 13 illustrates a preferred hair regeneration composition for males.

TABLE 13

HAIR REGENERATION COMPOSITION (MALES)

| | |
|---|---|
| Ketoconazole | 1 |
| PX-13 | 5 |
| Thymosin fraction 5 | 0.1 |
| Diosgenin | 0.2 |
| Melatonin | 0.025 |
| Indole-3-carbinol | 0.1 |
| Fragrance | 1 |
| Phenoxyethanol | 6 |
| Skin absorption enhancer | 10 |
| Pregnenolone | 0.2 |
| DHEA | 0.1 |
| Querretin methyl chalcone | 1 |
| L-Thyroxine | 0.003 |
| Vehicle | q.s. |

The above ingredients are shown in weight percent, and are available from commercial suppliers such as Brooks, Sigma (St. Louis, Mo.) and Aldrich (Milwaukee, Wis.).

The following Table 14 provides a range of concentrations of ingredients that may be used in the hair regeneration composition for males.

TABLE 14

HAIR REGENERATION COMPOSITION (MALES)

| | |
|---|---|
| Ketoconazole | 0–10 |
| PX-13 | 0–50 |
| Thymosin fraction 5 | 0.01–10 |
| Diosgenin | 0–20 |
| Melatonin | 0–10 |
| Indole-3-carbinol | 0–20 |
| Fragrance | 0–10 |
| Phenoxyethanol | 0–90 |
| Skin absorption enhancer | 0–90 |
| Pregnenolone | 0–10 |
| DHEA | 0–10 |
| Querretin methyl chalcone | 0–50 |
| L-Thyroxine | 0–1 |
| Vehicle | q.s. |

The above ingredients are shown in weight percent, and are available from commercial suppliers such as Brooks, Sigma (St. Louis, Mo.) and Aldrich (Milwaukee, Wis.).

The following Table 15 shows a preferred formula for hair regeneration composition for females.

TABLE 15

HAIR REGENERATION COMPOSITION (FEMALES)

| | |
|---|---|
| Ketoconazole | 1 |
| PX-13 | 5 |
| Thymosin fraction 5 | 0.1 |
| Progesterone | 0.2 |
| Melatonin | 0.025 |
| Phenoxyethanol | 6 |
| Skin absorption enhancer | 10 |
| Fragrance | 1 |
| Indole-3-carbinol | 0.1 |
| Pregnenolone | 0.2 |
| DHEA | 0.1 |
| Querretin methyl chalcone | 1 |
| L-Thyroxine | 0.003 |
| Vehicle | 2.5 |

The above ingredients are shown in weight percent, and are available from commercial suppliers such as Brooks, Sigma (St. Louis, Mo.) and Aldrich (Milwaukee, Wis.).

The following Table 16 provides a range of concentrations of ingredients that may be used in the hair regeneration composition for females.

TABLE 16

HAIR REGENERATION COMPOSITION (FEMALES)

| | |
|---|---|
| Ketoconazole | 0–10 |
| PX-13 | 0–50 |
| Thymosin fraction V | 0.01–10 |
| Progesterone | 0–20 |
| Melatonin | 0–10 |
| Phenoxyethanol | 0–90 |
| Skin absorption enhancer | 0–90 |
| Fragrance | 0–10 |
| Indole-3-carbinol | 0–20 |
| Pregnenolone | 0–20 |
| DHEA | 0–20 |
| Querretin methyl chalcone | 0–50 |
| L-Thyroxine | 0–1 |
| Vehicle | q.s. |

The above ingredients are shown in weight percent, and are available from commercial suppliers such as Brooks, Sigma (St. Louis, Mo.) and Aldrich (Milwaukee, Wis.).

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A hair regeneration composition comprising a thymic extract in an amount ranging from 0.1 to 10 percent by weight wherein the thymic extract is thymosin α1 or thymosin β4 or a combination thereof and at least one component which is selected from the group consisting of a steroid; an indole-based compound selected from the group consisting of indole, melatonin, N-[2-(5-Methoxy-1H-indol-3-yl) ethyl]acetamide, skatole and indole-3-carbinol; a mitocide; a bioflavanoid; an antiffungal compound selected from the group consisting of undecylenic acid, griseofulvin, terbinafine and an azole compound; and an anti-inflammatory fatty acid.

2. The composition of claim 1 wherein the thymic extract is thymosin fraction 5 (TF5).

3. The composition of claim 1 wherein the steroid is progesterone, pregnenolone, spironolactone, dehydroepiandrosterone (DHEA), or testolactone.

4. The composition of claim 1 wherein the mitocide is a solution of surfactant, fragrance and skin penetrant.

5. The composition of claim 4 wherein the fragrance is menthol, benzyl alcohol, eugenol, phenoxyethanol, isopropyl palmitate, isopropyl myristate, benzyl salicylate, phenylethyl salicylate, thymol, isoamyl salicylate, phenylethyl salicylate, benzoic acid, benzyl benzoate, methyl salicylate, phenol, oleic acid, caproic acid or carbaryl.

6. The composition of claim 1 wherein the bioflavanoid is querretin methyl chalcone.

7. The composition of claim 1 wherein the azole compound is ketoconazole or fluconazole.

8. A method for treating alopecia on the scalp of a patient in need thereof, comprising the steps of: cleansing the scalp with a cleansing agent; treating the cleansed scalp with a keratin solvent system; applying an acid peel solution to the keratin treated scalp; and applying a hair regeneration composition to the acid-peeled scalp, wherein the hair regeneration composition comprises a thymic extract in an amount ranging from 0.1 to 10 percent by weight, wherein the thymic extract is thymosin α1, thymosin β4 or a combination thereof.

9. The method of claim 8 wherein the hair regeneration composition further comprises at least one component which is selected from the group consisting of a steroid; an indole compound selected from the group consisting of indole, melatonin, N-[2-(5-Methoxy-1H-indol-3-yl)ethyl] acetamide, skatole and indole-3-carbinol; a mitocide; a bioflavanoid; an anti-fungal compound selected from the group consisting of undecylenic acid, griseofulvin, terbinafine and an azole compound; and an anti-inflammatory fatty acid.

10. The method of claim 8 wherein the cleansing agent is a cleansing shampoo.

11. The method of claim 10 wherein the cleansing shampoo is a hard-surface ethoxylated cleanser.

12. The method of claim 8 wherein the keratin solvent system is an acetic acid-based formula or a urea-based gel formula.

13. The method of claim 12 wherein the urea-based gel formula comprises at least one of the following: urea, citric acid, urea-peroxide, propylene glycol, ethoxylated alcohols or acrylic acid copolymer.

14. The method of claim 8 further comprising the step of applying a topical anesthetic prior to application of the acid peel solution.

15. The method of claim 14 wherein the topical anesthetic is a fragrance.

16. The method of claim 14 wherein the hair regeneration composition further comprises a surfactant or a solubilization agent.

17. The method of claim 8 wherein the acid peel solution comprises at least one physiological acid.

18. The method of claim 17 wherein the physiological acid is citric acid, ascorbic acid or pyruvic acid.

19. The method of claim 8 wherein the acid peel solution is allowed to remain on the scalp for about 1 minute.

20. The method of claim 8 wherein the acid peel solution is allowed to remain on the scalp for about 1 hour and an occlusive cap is placed over the scalp.

21. The method of claim 8 wherein the acid peel solution is allowed to remain on the scalp for up to about 8 hours and an occlusive cap is placed on head covering the scalp.

22. The method of claim 8, further comprising the step of applying a hyperactive urea gel formulation to solubilize bumps present on the surface of the scalp prior to application of the hair regeneration composition.

23. The method of claim 22 wherein the hyperactive urea gel formulation is at least one of the following: urea, citric acid, urea-peroxide, 2-phenoxyethanol, propylene glycol, or ethoxydiglycol.

24. The method of claim 9 wherein the steroid is progesterone, pregnenolone, spironolactone, dehydroepiandrosterone (DHEA), or testolactone.

25. The method of claim 9 wherein the mitocide is a solution of surfactant, fragrance and skin penetrant.

26. The method of claim 25 wherein the fragrance is menthol, benzyl alcohol, eugenol, phenoxyethanol, isopropyl palmitate, isopropyl myristate, benzyl salicylate, phenylethyl salicylate, thymol, isoamyl salicylate, phenylethyl salicylate, benzoic acid, benzyl benzoate, methyl salicylate, phenol, oleic acid, caproic acid or carbaryl.

27. The method of claim 9 wherein the bioflavanoid is querretin methyl chalcone.

28. The method of claim 9 wherein the azole compound is ketoconazole or fluconazole.

* * * * *